(12) United States Patent
Horwitz et al.

(10) Patent No.: US 6,867,219 B2
(45) Date of Patent: Mar. 15, 2005

(54) ANTITUMOR AGENTS

(75) Inventors: Jerome P. Horwitz, Farmington Hills, MI (US); Stuart T. Hazeldine, Taylor, MI (US); Thomas H. Corbett, Grosse Pointe Park, MI (US); Lisa Polin, Oak Park, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 10/210,781

(22) Filed: Jul. 31, 2002

(65) Prior Publication Data

US 2003/0144321 A1 Jul. 31, 2003

Related U.S. Application Data

(60) Provisional application No. 60/309,144, filed on Jul. 31, 2001.

(51) Int. Cl.[7] ............... A61K 31/47; C07D 215/227
(52) U.S. Cl. ............... 514/312; 546/157; 546/153
(58) Field of Search ............... 546/157; 514/312

(56) References Cited

U.S. PATENT DOCUMENTS

| | | | |
|---|---|---|---|
| 4,629,493 A | 12/1986 | Ura et al. | 71/92 |
| 5,250,690 A | * 10/1993 | Turner et al. | 544/354 |
| 5,364,831 A | 11/1994 | Yasukazu et al. | 504/235 |
| 6,197,728 B1 | 3/2001 | Yasukazu et al. | 504/235 |

OTHER PUBLICATIONS

Draetta et al. "Section V. Topics in Biology", Annual Reports in Medicinal Chemistry, 31, 1996, Academic Press, San Diego, pp 241–246.*
Salmon et al., "Principles of Cancer Therapy", Oncology, XIV, pp 1036–1049, 1999.*
Balasubramanian et al. "recent Developments in Cancer, etc.," Annual Reports in Medicinal Chemistry, 33, 1998, Academic Press, San Diego, pp 151–159.*

Hazeldine, Stuart T., et al., "J. Med. Chem. 2001, 44", Design, Synthesis, and Biological Evaluation of Analogues of Design, Synthesis, and Biological Evaluation of Analogues of the Antitumor Agent, 2–(4– [(7–Chloro–2–quinoxalinyl)oxy]phenoxy)proplonic Acid (XK469), (2001), p. 1758–1776.

Hazeldine, Stuart T., et al., "J. Med. Chem. 2002, 45", II, Synthesis and Biological Evaluation of Some Bioisosteres and Congeners of the Antitumor Agent, 2–(4– [97–Chloro–2–quinoxalinyl)oxy]phenoxylproplonic Acid(XK469), (2002), p. 3130–3137.

Corbett, Thomas , et al., "Preclinical Antitumor Efficacy of Analogs of XK469:sodium–(s–{4–(7–chloro–2–quinoxalinyloxy) phenoxy}propionate", Investigational New Drugs, (1998), 129–139.

* cited by examiner

Primary Examiner—Evelyn Mei Huang
(74) Attorney, Agent, or Firm—Schwegman, Lundberg, Woessner & Kluth, P.A.

(57) ABSTRACT

The invention provides compounds of formula I:

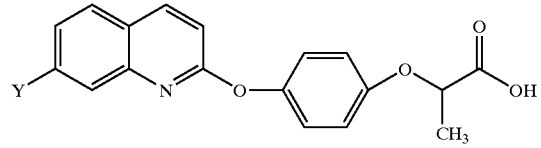

(I)

wherein Y is F, Cl, Br, methyl or methoxy; and pharmaceutically acceptable salts thereof. The compounds are effective antitumor agents. The invention also provides pharmaceutical compositions comprising a compound of formula I or a salt thereof, intermediates useful for preparing a compound of formula I, and therapeutic methods comprising administering a compound of formula I or a salt thereof to a mammal in need thereof.

31 Claims, 1 Drawing Sheet

ANTITUMOR AGENTS

PRIORITY OF INVENTION

This application claims priority of invention under 35 U.S.C. §119(e) from U.S. Provisional Application Ser. No. 60/309,144, filed Jul. 31, 2001, which is incorporated herein by reference.

GOVERNMENT FUNDING

The invention described herein was made in part with government support under NCI-NIH Grant Number CA82341 awarded by the National Cancer Institute. The United States Government has certain rights in the invention.

BACKGROUND OF THE INVENTION

U.S. Pat. No. 4,629,493 discloses herbicidal compounds of the following formula:

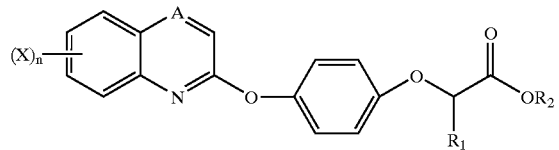

wherein A is —CH— or —N—; X is a halogen; n is 0,1, or 2; $R^1$ is hydrogen or a lower alkyl group; and $R^2$ is —OH, among other values. One of these compounds is currently sold commercially for the control of annual and perennial grass weeds in broadleaf crops. This compound has the following formula:

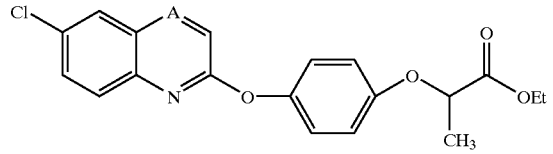

Corbett et. al., *Investigational New Drugs*, 16 129–139 (1998) evaluated a series of quinoxaline compounds for activity against solid tumors in mice. The following compound (referred to as XK469) was reported to have broad activity against transplantable mouse tumors.

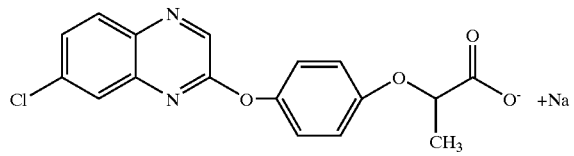

The compound was also reported to have a relatively low potency, and to produce several undesirable side effects, including in vivo toxicity, e.g., paralytic ileus, GI-epithelial damage, marrow toxicity, neuromuscular toxicity and weight loss. There is currently a need for additional antitumor agents.

SUMMARY OF THE INVENTION

The present invention provides compounds that are effective antitumor agents. Accordingly, there is provided a compound of the invention which is a compound of formula I:

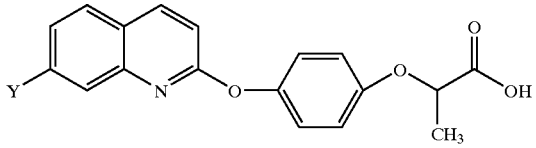

wherein Y is F, Cl, Br, methyl or methoxy; or a pharmaceutically acceptable salt thereof.

The invention also provides a therapeutic method to inhibit tumor cell growth in a mammal, comprising administering to a mammal in need of such therapy, an effective amount of a compound of the invention.

The invention also provides a therapeutic method to treat cancer in a mammal, comprising administering to a mammal in need of such therapy, an effective amount of a compound of the invention.

The invention also provides the use of a compound of the invention in medical therapy.

The invention also provides the use of a compound of the invention to manufacture a medicament for the treatment of cancer in a mammal.

DETAILED DESCRIPTION OF THE INVENTION

Figure 1:
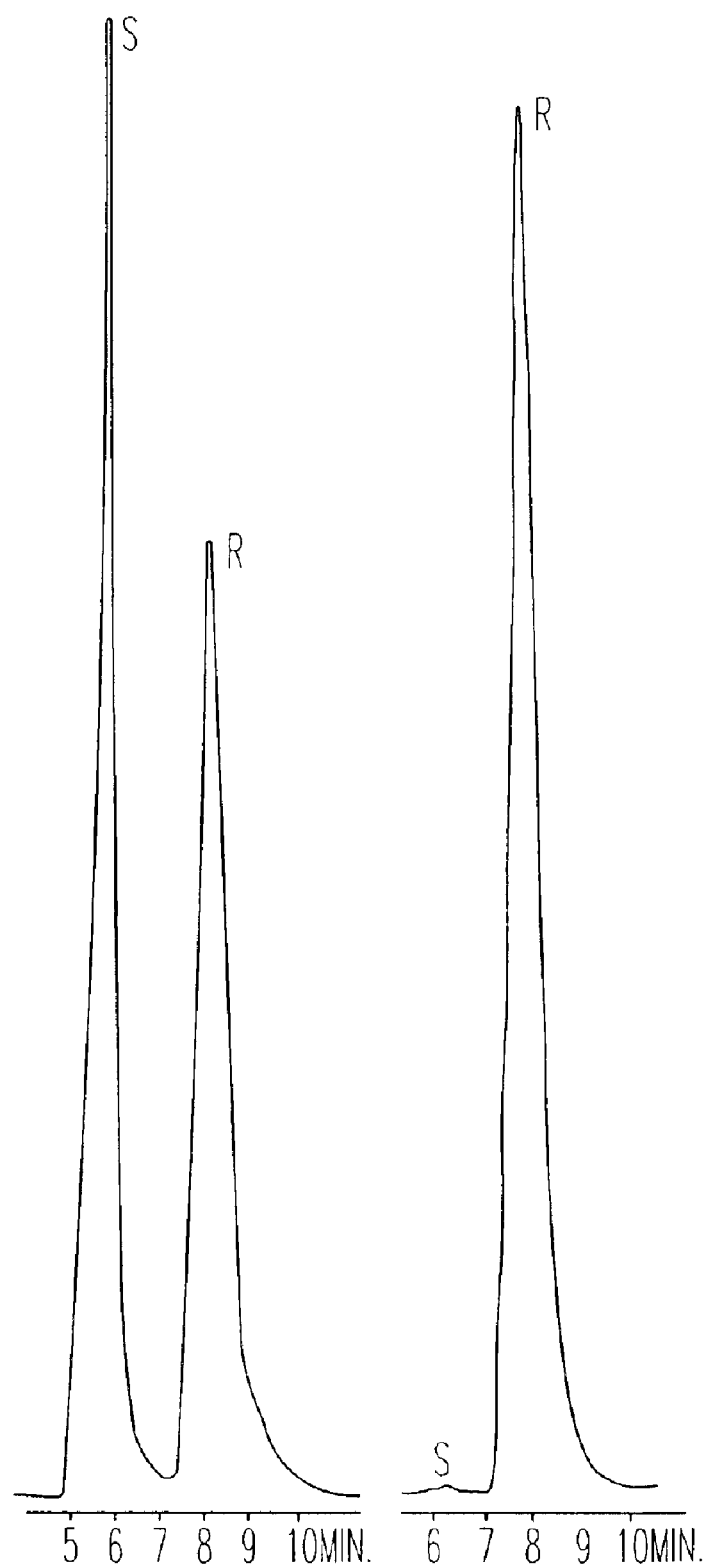
FIG. 1 shows HPLC separations of racemic compound 21b (Scheme II) and the R-enantiomer of compound 21b using Chirobiotic T250×4.6 mm, 65% $H_2O$, 35% $CH_3OH$, 20 mM $NH_4NO_3$ at 1 mL/min with detection at 250 nm.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antitumor activity using the standard tests described herein, or using other similar tests which are well known in the art.

A specific value for Y is fluoro.

Another specific value for Y is chloro.

Another specific value for Y is bromo.

Another specific value for Y is methoxy (—OMe)

A specific group of compounds of Formula I are compounds wherein the carbon bearing the methyl group is in the (S) configuration.

A preferred group of compounds of Formula I are compounds wherein the carbon bearing the methyl group is in the (R) configuration.

Preferred compounds of the invention are 2-[4-(7-chloroquinolin-2-yloxy)phenoxy]propanoic acid (compound 21b); 2-[4-(7-bromoquinolin-2-yloxy)phenoxy] propanoic acid (compound 21c); 2-[4-(7-fluoroquinolin-2- yloxy)phenoxy]propanoic acid (compound 21a) and the pharmaceutically acceptable salts thereof (e.g., compounds 22a, 22b and 22c). More preferably, the compounds of the invention are (R) 2-[4-(7-chloroquinolin-2-yloxy)phenoxy] propanoic acid (compound 21b), or a pharmaceutically acceptable salt thereof (e.g., compound 22b), and (R) 2-[4-(7-bromoquinolin-2-yloxy)phenoxy]propanoic acid (compound 21c), or a pharmaceutically acceptable salt thereof (e.g., compound 22c).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, dimethyl sulfoxide (DMSO), alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound is conveniently administered in unit dosage form; for example, containing 5 to 1000 mg/m$^2$, conveniently 10 to 750 mg/m$^2$, most conveniently, 50 to 500 mg/m$^2$ of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of the invention are effective anti-tumor agents and have higher potency and/or reduced toxicity as compared to XK 469. Preferably, compounds of the invention are more potent and less toxic than (R) XK 469, and/or avoid a potential site of catabolic metabolism encountered with XK469, i.e., have a different metabolic profile than XK469.

The present invention provides therapeutic methods of treating cancer in a mammal, which involve administering to a mammal having cancer an effective amount of a compound or a composition of the invention. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumors screens are documented. In addition, ability of a compound to treat cancer may be determined using the Tests as described below.

In Tests A–H the following general methodologies were employed:

Tumor and Animal Maintenance

Pancreatic ductal adenocarcinoma-03, B16-melanoma, mammary adenocarcinoma-16/C/Adr, mammary adenocarcinoma-17/Adr, colon adenocarcinoma-26, and mammary adenocarcinoma-16/C were used in the studies. Tumors were maintained in the mouse strain of origin C57B1/6 (for Panc03, B16), Balb/c (for Colon 26) and C$_3$H (for the mammary tumors). Tumors were transplanted into the appropriate F$_1$ hybrid (BDF1=C57B1/6 female X DBA/2 male) or the strain of origin for the chemotherapy trials. Individual mouse body weights for each experiment were within 5 grams, and all mice were over 17 grams at the start of therapy. The mice were supplied food and water ad libitum.

Chemotherapy of Solid Tumors

Animals were pooled, implanted subcutaneously with 30 to 60 mg tumor fragments by a 12 gauge trocar on day 0, and again pooled before unselective distribution to the various treatment and control groups. For early stage treatment, chemotherapy was started within 1 to 3 days after tumor implantation while the number of cells was relatively small ($10^7$ to $10^8$ cells). For upstaged or advanced staged trials, the tumors were allowed to grow for five or more days before treatment was started. Tumors were measured with a caliper twice weekly. Mice were sacrificed when their tumors reached 1500 mg. Tumor weights are estimated from two-dimensional measurements:

Tumor weight (in mg)=$(a \times b^2)/2$, where a and b are the tumor length and width in (mm), respectively.

End Points for Assessing Antitumor Activity for Solid Tumors

The following quantitative endpoints were used to assess antitumor activity:

a) Tumor growth delay (T–C value), where T is the median time (in days) required for the treatment group tumors to reach a predetermined size (e.g., 1000 mg), and C is the median time (in days) for the control group tumors to reach the same size. Tumor-free survivors were are excluded from these calculations (cures are tabulated separately). This value is an important criterion of antitumor effectiveness because it allows the quantification of tumor cell kill.

b) Calculation of tumor cell kill For subcutaneously (SC) growing tumors, the $\log_{10}$ cell kill was calculated from the following formula:

$$\text{The } \log_{10} \text{ cell kill total (gross)} = \frac{T - C \text{ value in days}}{(3.32)(Td)}$$

where T–C is the tumor growth delay as described above and Td is the tumor volume doubling time (in days), estimated from the best fit straight line from a log-linear growth plot of the control group tumors in exponential growth (100 to 800 mg range). The conversion of the T–C values to $\log_{10}$ cell kill is possible because the Td of tumors regrowing post treatment (Rx) approximates the Td values of the tumors in untreated control mice.

The issue of conversion of tumor growth delay (T–C value) to log tumor cell kill is justified in this series because of the large number of cures obtained with 5 of the agents studied. Cures are a clear indication of tumor cell kill (rather than stasis of tumor cell replication).

In selected cases, both for historic in vivo evaluation data as well as data presented here, it is of value to compare log kill numbers from trials of markedly different testing schedules. For this purpose, an activity table was created, and is presented below. It should be noted that an activity rating of +++ to ++++ is needed to effect partial regression (PR) or complete regression (CR) of 100 to 300 mg size masses of most transplanted solid tumors of mice. Thus, an activity rating of + or ++ would not be scored as active by usual clinical criteria. A PR is a reduction in tumor mass to less than 50% of pretreatment size. A CR is a reduction in tumor mass to below palpable size (i.e., reduction to zero detectable mass).

Conversion of $\log_{10}$ tumor cell kill to an activity rating

| Antitumor activity | | Duration of Rx 5 to 20 days $\log_{10}$ kill (gross) |
|---|---|---|
| Highly active | ++++ | >2.8 |
| | +++ | 2.0–2.8 |
| | ++ | 1.3–1.9 |
| | + | 0.7–1.2 |
| | − | <0.7 |

The treatment and control groups were measured when the control group tumors reach approximately 700 to 1200 mg in size (median of group). The T/C value in percent is an indication of antitumor effectiveness: A T/C=0% means no tumor growth. A T/C=100% means no antitumor activity, i.e., the treated and control tumors grew equally. A T/C equal to or less than 42% is considered significant antitumor activity by the Drug Evaluation Branch of the Division of Cancer Treatment (NCI). A T/C value <10% is considered to indicate highly significant antitumor activity, and is the level used by NCI to justify a clinical trial if toxicity, formulation, and certain other requirements are met (termed DN-2 level activity). A body weight loss nadir (mean of group) of greater than 20% or greater than 20% drug deaths is considered to indicate an excessively toxic dosage in most single course trials.

Drug Preparation for Injections in Mice

Compound 22b (sodium salt) in Tests A–H was prepared in a 1% sodium bicarbonate solution, $dH_2O$ or phosphate buffered saline (PBS), with pH adjusted to 7.0 to 7.5 with HCl, and administered intravenously (IV) or orally (PO), at injection volumes of 0.2 ml per injection.

Test A

Evaluation Against Early Stage Pancreatic Ductal Adenocarcinoma 03

The pancreatic ductal adenocarcinoma 03 tumor is highly sensitive to taxol (++++ activity rating). It is sensitive to adriamycin (+++ activity rating), moderately sensitive to VP-16, cytoxan, and CisDDPt (++ activity rating), and modestly sensitive to 5-FU (+ activity). Female BDF1 mice (obtained from NCI-Raleigh) (date of birth (hereinafter D.O.B.) Mar. 27, 2000; date of arrival (hereinafter D.O.A.) Apr. 9, 2000) were implanted (tumor implant date (hereinafter D.O.T.) Mar. 17, 2000) with pancreatic ductal adenocarcinoma 03 tumor, divided into treatment and control groups. The treatment group was administered compound 22b each day on days 3–9 IV. The results of Test A are summarized in Table 1.

Test B

Evaluation Against Early Stage B16 Melanoma

B16 melanoma is a very drug insensitive tumor when implanted subcutaneously (SC) It is unresponsive to VP-16, vinblastine, and Ara-C (negative (−) activity rating), marginally responsive to taxol, adriamycin and camptothecin (+ or +/− activity rating), modestly responsive to 5-FU, cytoxan, and CisDDPt (++ activity rating). Only BCNU and other nitrosoureas are highly active (++++ activity rating).

BDF1 female mice (obtained from NCI-CRL-Ral) (D.O.B. Jan. 24, 2000, D.O.A. Feb. 29, 2000). The average weight of the mice was 21.6 gm. Mice were implanted with B16 melanoma cells, passage number 138 (D.O.T. Apr. 17, 2000). Td (tumor volume doubling time) was 1 day. The mice were divided into a control group and three experimental groups. The control group (Cage #1) received no treatment.

Cage #1 reached 1000 mg in 7 days (1.0 day Td), and tumor growth was as expected.

In Cage #2, compound 22b (racemic) was administered IV at 40 mg/kg/injection, once per day on days 1–4. A total of 320 mg/kg was administered. This dose was toxic, producing 1/5 drug deaths (occurring on day 7). The cause of death was marrow toxicity, as evidenced by a small spleen size. Examination of the gastrointestinal tract revealed it was empty, indicating no food intake prior to death. This dose produced severe weight loss (−20.8%; nadir occurred on day 7 with full recovery on day 11). A −20% body weight loss is considered excessively toxic by N.C.I. standards. Here, administration of compound 22b (racemic) was associated with a slowing of nerve conduction in the mice. At doses of 50 mg/kg, the toxicity was mild, but lasted for 20 minutes on day 1, and for 8 minutes on day 4. At high dosages, e.g., 80 mg/kg, the agent produced a substantial post injection neuromuscular toxicity lasting for over 20 minutes but resolved by two hours. This included a distinctive paralysis of the hind legs, indicating that the toxicity was related to the conduction velocity, since the longer the nerves, the more function was affected. As will be discussed later, this slowing of nerve conduction occurs with the racemic and S-enantiomer of this series. In all cases, it is absent in the R-enantiomeric forms.

In Cage #3, compound 22b was administered IV at 50 mg/kg/injection, daily on days 1–5. A total of 250 mg/kg were administered. At this dose, the percentage of body weight loss was −13% (nadir occurred on day 7, full recovery on day 11, for a four day host recovery time). This dose was active (T/C=0, 2.6 log kill, +++ activity rating).

In Cage #4, compound 22b was administered IV, at 30 mg/kg/injection daily on days 1–6 for a total administration of 180 mg/kg. This dose produced a −7.4% body weight loss (nadir occurred on day 5, with a full recovery on day 9). This dose was active (T/C=15.6%, 1.8 log kill, ++ activity rating).

The results of Test B are summarized in Table 2.

Test C

Evaluation Against Early Stage Mammary Adenocarcinoma-16/C/Adr

Early stage mammary adenocarcinoma-16/C/Adr is a p-glycoprotein negative multidrug resistant tumor. C3H female mice were obtained from NCI-Kingston-CRL (D.O.B. Apr. 3, 2000; D.O.A. May 16, 2000). The average weight of the mice was 26.3 gm. Mice were implanted with early stage mammary adenocarcinoma-16/C/Adr passage number 183 and divided into a control group (Cage #1) and two experimental groups (Cage #2 and Cage #3) (D.O.T.= Jun. 22, 2000). The control animals (Cage #1) received no treatment. The racemic form of compound 22b (chloro analog) was administered to the experimental groups as follows:

| Group | Treatment regime |
|---|---|
| Cage #2 | 42 mg/kg compound 22b; twice daily on days 1–3 and 11–13 with a four hour split |
| Cage #3 | 27 mg/kg compound 22b; twice daily on days 1–3 and 11–13 with a four hour split |

Cage #1 reached 1000 mg in 16 days (1.2 day Td), and tumor growth was as expected.

In Cage #2, a total administration of 504 mg/kg compound 22b was administered by IV This treatment produced a modest neuromuscular gait disturbance lasting for about ten minutes post injection. The toxicity was most evident the first two days, becoming less evident with subsequent injections. This dose produced a −15% body weight loss (nadir occurred on day 7, and full recovery occurred on day 12). Interestingly, the mice gained weight during the second course of treatment (days 11–13). The agent was active at this dose (T/C=0%, 2.0 log kill, +++ activity rating).

In Cage #3, a total of 324 mg/kg compound 22b was administered. This dose produced an insignificant gait disturbance, and a −1.1% loss of body weight in the Cage #3 animals (nadir occurred on day 7, and full recovery occurred on day 8). The agent was inactive at this dose schedule (T/C=53%, 0.6 log kill). The results of Test C of are summarized in Table 3.

Test D

Evaluation of Racemic Compound 22c Against Early Stage Mammary Adenocarcinoma-17/Adr A racemic mixture of compound 22c (bromo analog) was evaluated against a multidrug-resistant mammary tumor (Maim-17/Adr).

Female C3H/HeN (MTV-neg) mice were obtained from N.C.I. Frederick (D.O.B. was Oct. 9, 2000; D.O.A. was Nov. 14, 2000). The mice weighed an average of 29.3 gm. Mice were implanted with Mam-17/Adr/passage-220 (a p-glycoprotein positive multidrug-resistant-tumor) (D.O.T. was Jan. 2, 2001; Td=1.0 days). Compound 22c (racemic) was prepared for administration by suspending in 5% ethanol, 1% POE-80, and 1% sodium bicarbonate to effect solution. Then, P.B.S. was added, and the pH was adjusted to 7 with HCl. 0.2 ml per injection was administered IV.

Cage #1 animals received no treatment. Tumor growth as expected, reaching 1000 mg on day 7 (range 7–9) (Td=1.0 days).

Animals in cage #3 were administered the racemic preparation of compound 22c by IV at 50 mg/kg/injection on day 1; 62.5 mg/kg on day 2; and 60 mg/kg/injection on days 3, 6, 7, 8 for a total of 352.5 mg/kg. This dose produced a modest −5.5% body wt loss. This agent caused a modest slowing of nerve conduction, lasting approximately 10 minutes at the 60 to 62.5 mg/kg dose. The symptoms were a mild gait disturbance. This dose had impressive antitumor activity (T/C=0, 4.2 log kill, ++++ activity rating). The tumors reached 1000 mg on day 21 (range 19–42). No antitumor agent, standard or investigation has exceeded this degree of activity against this tumor.

Cage #4 animals were given the racemic preparation of compound 22c by IV at 30 mg/kg on day 1; 37.5 mg/kg on day 2; and 36 mg/kg/injection on days 3, 6, 7, 8 for a total of 211.5 mg/kg. There was no gait disturbance at this dose. This dose was also highly active (3.0 log kill). The tumors reached 1000 mg on day 17 (range 14–21).

The racemic preparation of compound 22c was found to have the same type of neuromuscular toxicity observed in testing a racemic preparation of compound 22b, but it was less severe (see Test B).

Results are presented in Table 4.

Test E

Evaluation of the R-Enantiomer of Compound 22b and Compound 22a Against Early Stage Mammary Adenocarcinoma-17/Adr The activity of the R-enantiomer of compound 22b and compound 22a (fluoro analog) were evaluated for activity against mammary tumor Mam-17/Adr, which is a p-glycoprotein positive multidrug-resistant-tumor. C3H/HeN (MTV-neg) female mice were obtained from N.C.I.-Frederick (D.O.B. was Nov. 20, 2000; D.O.A. was Jan. 2, 2001). The average weight of the mice was 25.9 gm. Mice were implanted with Mam-17/Adr/passage-223 (D.O.T. was Feb. 12, 2001; Td was 1.2 days) and divided into a control and treatment groups.

A racemic preparation of compound 22a was suspended in 3% ethanol, 1% POE-80, and 0.25% sodium bicarbonate to effect solution. Then, P.B.S. was added and the pH adjusted to 7 with HCl. A volume of 0.2 ml per injection was administered to animals intravenously. The R-enantiomer of compound 22b was suspended in 3% ethanol, 1% POE-80, and 0.5% sodium-bicarbonate to effect solution. Then, P.B.S. was added and the pH was adjusted to 7 with HCl. A volume of 0.2 ml per injection was administered to animals intravenously.

Cage #1, the control group, received no treatment, and reached 1000 mg in 9.0 days (8.5–10), (1.2 day Td). The tumor growth was as expected.

Cage #3 was administered 36 mg/kg of racemic compound 22a by IV on day 1, and 48 mg/kg/injection qd-2–7 for a total of 324 mg/kg. Higher individual dosages could not be given because of severe neuromuscular toxicity (slowing in nerve conduction resulting in dysfunctional leg movements, both front and rear. The dysfunction lasted for 15 minutes for the front legs and longer for the rear legs. This dose was active (T/C=14%, 1.5 log kill, ++ activity rating). Although active, this is clearly not an improvement over compound 22b or compound 22c.

Cages #4 and #5 received lower doses of the racemic compound 22a preparation than Cage #3. These were inactive.

Cage #6 were administered an R-enantiomer of compound 22b and neuromuscular toxicity was not produced. In Test B, the racemic form of compound 22b produced a slowing in nerve conduction. This result implied that the S-enantiomer is responsible for the neuromuscular toxicity of compound 22b. The S-enantiomeric form was later synthesized and injected at 80 mg/kg/injection and also at 50 mg/kg/injection, IV, both producing marked neuromuscular toxicity. In Cage #6, the R-enantiomer of compound 22b was injected IV at 83 mg/kg/injection, qd-1–4 for a total of 332 mg/kg. This dose was toxic, killing all of the 5 mice (on days 7, 7, 8, 9, 10). The cause of death was GI-epithelial damage producing GI-epithelial slough resulting in diarrhea. Three of the mice had slightly enlarged food-filled stomachs, indicating gastroparesis or paralytic ileus. The spleen sizes for all of the mice were near normal, indicating that the agent did not produce much marrow toxicity in the mice.

Cage #7 were administered the R-enantiomer of compound 22b by IV at 55 mg/kg/injection, qd-1–4 for a total dose of 220 mg/kg. This dose was somewhat toxic, producing 1/5 drug deaths and a large body weight loss (−23.4% nadir day 9 and full recovery on day 14). The one death was from GI-epithelial damage (diarrhea) complicated with marrow toxicity (small spleen). This dose was, however, highly active (T/C=0, 3.3 log kill, ++++ activity rating). The tumors reached 1000 mg on day 22 (18–23).

Cage #8 contained only one mouse, which was used for an initial toxicity control to evaluate neuromuscular toxicity. It was injected with a single bolus dosage of the R-enantiomer of compound 22b preparation at 124.5 mg/kg on day 1 only. There was no neuromuscular toxicity. The dose was modestly active and not toxic (T/C=35%, 0.8 log kill, + activity rating).

Thus, the data indicated that compound 22a was active (Cage #2). The R-enantiomer of compound 22b was devoid of the neuromuscular toxicity that occurs with the racemic form of the agent. The S-enantiomer was made and tested and found to be responsible for the neuromuscular toxicity.

Results are presented in Table 5.

Test F

Evaluation of the R-Enantiomer of Compound 22b and the R-Enantiomer of Compound 22c Against Early Staged Mammary Adenocarcinoma-16/C In this trial, the R-enantiomers of both compound 22c and compound 22b were compared. Each compound was completely devoid of neuromuscular toxicity. The lethal dose-limiting toxicities are similar (GI epithelial damage).

C3H female mice were obtained from N.C.I. (D.O.B. was Jan. 22, 2001; D.O.A. was Jan. 27, 2001). The mice weighed an average of 19.2 gm. Mice were implanted SC with mammary adenocarcinoma-16/C passage-170, a fast growing, highly invasive, highly metastatic tumor (D.O.T. was Mar. 8, 2001; Td was 1.2 days).

The R-enantiomers of both Compound 22c and Compound 22b were each suspended in 3% ethanol, 1% POE-80, 0.5% sodium bicarbonate (by volume) to effect solution, P.B.S. was then added and the pH adjusted to 7 with HCl. Adriamycin (ADRIA; lot number 20338c) was suspended in $dH_2O$ to effect solution and the pH was adjusted to 6.0. Mice were administered 0.2 ml per IV injection.

Cage #1 received no treatment, and tumor growth was as expected. The tumors reached 1000 mg on day 9.5 (range 7–12) (Td=1.0 days).

Cage #2 mice were administered the R-enantiomer of compound 22c by IV at 65 mg/kg/inj qd-1–4 for a total of 260 mg/kg. No neuromuscular toxicity occurred following the injections. All the mice died 2–3 days following the last treatment from G.I. epithelial damage.

Cage #3 mice were administered R-enantiomer of compound 22c by IV at 65 mg/kg/injection every other day (once each on days 1, 3, 5, 7) for a total of 260 mg/kg. In keeping with a very rapid host recovery time for this analog series, there were no deaths. The mice encountered a −8.3% body weight loss (nadir day 9 with full recovery day 12), indicating that the total dose on this intermittent schedule was adequate, but not excessive. Again, there was no neuromuscular toxicity with this dose-schedule. This dose was active (T/C=4%; 1.7 Log kill; ++ activity rating).

Cage #4 mice were administered the R-enantiomer of compound 22c by IV at 40 mg/kg/injection on the same schedule as in Cage#3 (i.e., on days 1, 3, 5, 7) for a total of 160 mg/kg. There was no toxicity and the mice gained weight during treatment (+6.4% body weight gain). This dose was also active (T/C=9%; 1.4 Log kill; and ⅕ cures; ++ activity rating if the cure is not considered). The tumor free mouse was reimplanted with Mam16/C tumor on day 155. The implant grew successfully, indicating that immunogenic factors were not involved in the original cure.

Cage #5 mice were administered the R-enantiomer of compound 22b by IV at 50 mg/kg/inj qd-1–5 for a total of 250 mg/kg. No neuromuscular toxicity occurred post injections. This dose caused an excessive weight loss, but no deaths. The mice regained all the weight within 5 days (−22.9% body weight loss on day 8, with full recovery on day 13, indicating that some of the weight loss was from dehydration). This dose was highly active (T/C=0%; 2.1 Log kill; +++ activity rating).

Cage #6 mice were administered the R-enantiomer of compound 22b by IV at 50 mg/kg/injection on days 1, 3, 5, 7 for a total of 200 mg/kg. This dose was well tolerated, and caused no weight loss. It was active (T/C=5%; 1.7 Log kill; ++ activity rating). It is likely that a higher dose could be given on this schedule, considering the lack of weight loss.

Cage #7 mice were administered the R-enantiomer of compound 22b by IV at 30 mg/kg/injection on the same schedule as in Cage-6 for a total of 120 mg/kg. The mice gained weight. This dose was modestly active (T/C=32%; 0.8 Log kill; + activity rating).

Cage #11 mice were administered adriamycin as a positive control. Historically, adriamycin is one of the most active agents against this tumor. 7.5 mg/kg/injection was administered by IV on days 1 and 5, for a total of 15 mg/kg. While no body weight loss was observed, the mice did not begin to re-gain weight until day 11, and then only modestly. There was one delayed drug-death in this group. As expected, this agent was highly active (T/C=0%; 3.6 Log kill; ++++ activity rating, although at a toxic dose).

At dosages that produced less than 10% body weight loss, the R-enantiomer of compound 22b and the R-enantiomer of compound 22c were equally active, each with a 1.7 log kill (see Cages 3 and 6). At equal active dosages, the R-enantiomer of compound 22b had a slightly lower dose requirement (200 mg/kg—see Cage 6) than the R-enantiomer of compound 22c (260 mg/kg—see Cage 4).

Results are presented in Table 6.

Test G

Evaluation of the R-enantiomers of Compounds 22c and 22b Against Up-staged Pancreatic Ductal Adenocarcinoma-03

In this trial, the R enantiomers of Compound 22c and 22b were compared.

BDF1 female mice were obtained from N.C.I., CRL-Ral (D.O.B. was Feb. 26, 2001; D.O.A. was Mar. 10, 2001). The mice weighed an average of 22.5 gm. Mice were implanted SC with pancreatic ductal adenocarcinoma-03 passage 143. (D.O.T. was May 29, 2001; Td was 2.3 days).

The R-enantiomer of compound 22c was suspended in 3% ethanol, 1% POE-80, 0.25% sodium bicarbonate (by volume) to effect solution. $dH_2O$ was then added, and the pH adjusted to 7 with HCl. Mice were administered 0.2 ml per IV injection. The R-enantiomer of compound 22b was suspended in 3% ethanol, 1% POE-80, 0.5% sodium-bicarbonate (by volume) to effect solution. Then, dH2O was added, and the pH adjusted to 7.5 with HCl. Mice were injected with 0.2 ml per injection IV or PO. Adriamycin (source ADRIA; lot 2033BC) was suspended in dH2O to effect solution, and the pH was 6.0. Mice were administered 0.2 ml per IV injection.

Treatment began six days following implant, at which time the tumors were palpable size (126 mg median). The duration of treatment was prolonged (18 days) in order to obtain a clear separation in efficacy between the compounds.

Cage #1 received no treatment, and tumor growth was as expected. The tumors reached 1000 mg on day 16.5 (range 15–21; Td=2.3 days).

Cage #2 mice were administered compound 22b (R-enantiomer) by IV at 80 mg/kg/injection on an intermittent schedule (1×/day on days 6, 9, 12, 15, 18, 21, 24) for a total of 560 mg/kg. The regimen was well tolerated with no weight loss or deaths. The mice were agitated post IV injection, but the behavior lasted only a few minutes. There is no neuromuscular toxicity with the R-enantiomer. This dose was active (2.3 log kill, 2/7 PR's, +++ activity rating). This dose-schedule was clearly inferior to compound 22c (R-enantiomer).

Cage #3 mice were administered compound 22b (R-enantiomer) by IV at 50 mg/kg/inj on an intermittent schedule (1×/day on days 6,9,12,15,18,21,24) for a total of 350 mg/kg. The regimen was well tolerated with no weight loss or deaths. This dose was active (1.5 log kill, 1/6 CR's, ++ activity rating).

Cage #4 mice were administered compound 22b (R-enantiomer) by IV at 31 mg/kg/inj on an intermittent schedule (1×/day on days 6,9,12,15,18,21,24) for a total of 217 mg/kg. The regimen was well tolerated with substantial weight gain. This dose was not active (0.5 log kill,—activity rating).

Cage #5 mice were administered compound 22b (R-enantiomer) SC at 31.2 mg/kg/inj on a daily schedule (qd 6–24) for a total of 592.8 mg/kg. The regimen was well tolerated with only minor weight loss and no deaths. The mice were not agitated post SC injection. This dose was only modestly active (0.9 log kill, 1/5 CR's, + activity rating). The one tumor free mouse was reimplanted with 30 mg tumor fragments of P03 on day 157. The implant grew, indicating that immune factors were not involved in the original cure. This SC daily schedule was clearly inferior to the IV intermittent schedule (compare to cage #2).

Cage #6 mice were administered compound 22b (R-enantiomer) SC at 19.5 mg/kg/inj on a daily schedule (qd 6-24) for a total of 370.5 mg/kg. The regimen was well tolerated with no weight loss and no deaths. The mice were not agitated post SC injection. This dose was not active (0.4 log kill,—activity rating). This SC daily schedule was clearly inferior to the IV intermittent schedule (compare to cage #3).

Cage #12 mice were administered compound 22c (R-enantiomer). Only limited drug supply was available, thus only one dose level IV was tested, and only 4 mice per group could be used. Compound 22c was administered IV at 80 mg/kg/inj on an intermittent schedule (1×/day on days 6,9,12,15,18,21) for a total of 480 mg/kg. The day 24 injection was omitted because the drug supply was exhausted. The regimen was well tolerated with no weight loss and no deaths. The mice were agitated post IV injection, but the behavior lasted only a few minutes. There was slightly more agitation with this compound analog than occurred with compound 22b. There is no neuromuscular toxicity with the R-enantiomer. This dose was highly active (3.1 log kill, 3/4 complete regressions, ++++ activity rating). This dose-schedule with compound 22c was markedly superior to compound 22b against this pancreatic ductal adenocarcinoma.

Cage #13 mice were administered adriamycin as a positive control. Historically, adriamycin is a highly active agent against this tumor. A dosage of 7.5 mg/kg/injection was given IV days 6,14 for a total of 15 mg/kg (the approximate maximum tolerated dose). This was well tolerated in this trial, with no weight loss and no deaths. As expected, this agent was active, (2.3 log kill, 1/5 CR's, +++ activity rating).

Compound 22c-R-enantiomer was markedly superior to compound 22b on an intermittent dose schedule given IV. The intermittent schedule IV was clearly superior to the daily oral schedule.

Results are presented in Table 7.

Test H

Evaluation of the R-enantiomers of XK-469, Compound 22b, and Compound 22c Against Advanced Staged Colon Carcinoma 26 in Female Balb/c Mice In this trial the R-enantiomers of XK-469, compound 22c, and compound 22b were compared against advanced staged colon carcinoma 26 in female Balb/c mice. Compound 22c was markedly more active than compound 22b or compound XK469 against this colon carcinoma. Cage #2 was 22b at 400 mg/kg and Cage 4 was 22c at 400 mg/kg. Both were toxic and omitted from this table.

* The "*" asterisk indicates the tumor is highly metastatic and toxic, causing substantial body weight loss. In the treated groups, the weight loss was determined at a time before the tumor had a substantial impact.

The XK469-R, 22b, and 22c compound doses were all prepared the same, using 3% ethanol, 1% POE-80, and 0.5% sodium bicarbonate. The injection volume was 0.2 mL/mouse IV. Cytoxan was prepared in dH$_2$O and injected IV in a volume of 0.2 mL per mouse. The mice were Balb/c female mice: DOB Feb. 12, 2001; DOA Mar. 27, 2001; DOT Aug. 8, 2001, with an average body weight of 24.7 grams at the start of Rx administration. The tumor was Colon Carcinoma-26 passage 141; date of implant Aug. 8, 2001, and implanted at 30 to 60 mg fragments bilaterally SC. All tumors were 63 to 171 mg on day 6, the day of first Rx.

Cage #1: Control: growth as expected, 1.7 day Td.

Cage #3: 22b: 50 mg/kg/injection was given IV on days 6, 8, 10, 13, and 15 for a total of 250 mg/kg. This produced 1/6 complete regressions and a 1.4 log kill (++ activity rating).

Cage #5: 22c: 50 mg/kg/injection was given IV on days 6, 8, 10, 13, and 15 for a total of 250 mg/kg. This produced 3/6 complete regressions, and 3/6 tumor free survivors on day 55. These mice remained in excellent condition, gaining weight and skeletal size. They were reimplanted with 30 mg fragments of Colon-26 on day 156. The implants grew successfully, indicating that immune factors were not involved in the original cures (++++ activity rating).

Cage #6: XK469-R: 80 mg/kg/injection was given IV on days 6, 8, 10, 14, and 16 for a total of 400 mg/kg (The historic MTD is in the 400 to 450 mg/kg range). There were no regressions. This dosage produced 0.9 log kill (+ activity rating).

Cage #7: XK469-R: 50 mg/kg/injection was given IV on days 6, 8, 10, 13, and 15 for a total of 250 mg/kg. This dose was inactive.

Cage #8: Cytoxan was injected IV at 110 mg/kg per injection on days 6, and 10 for a total of 220 mg/kg. There was no meaningful activity. Historically Cytoxan is active against this tumor if treatment is started on day 1 (the day after implant).

The results are presented in Table 8.

The invention will now be illustrated by the following non-limiting examples:

EXAMPLE 1

Synthesis of [4-[(7-Substituted-2-quinolinyl)oxy]phenoxy]-propionic Acids (Schemes I-III)

As shown in Scheme I, a one-pot preparation of trans-3-ethoxyacryloyl chloride (4) by reaction of ethyl vinyl ether (2) and oxalyl chloride (3), with subsequent decarboxylation, has been described by Tietze et al., *Synthesis*, 1079–1080 (1993). The amidation of the meta-substituted anilines (5a–e) with 4, i.e., the conversion to 6a–e, was modeled after the procedure described by Campbell and Roberts (U.S. Pat. No. 4,710,507) for preparation of trans-N-(4-bromo-3-methylphenyl)-3-ethoxypropenamide. Cyclization of the latter to a mixture of 5-(8a-3) and 7-substituted quinolin-2-ols (7a–e) was effect in either concentrated sulfuric or hydrochloric acid (Campbell and Roberts). The mixture, in turn, was transformed to the corresponding 2-chloroquinoline derivatives (9a–e) and (10a–e), on refluxing with phosphorous oxychloride (Campbell and Roberts). The majority of the 7-substituted derivatives (9a–e) separated from the regioisomer (10a–e) on fractional crystallization. The residue yielded additional 9a–c, following column chromatography over silica gel.

Scheme I

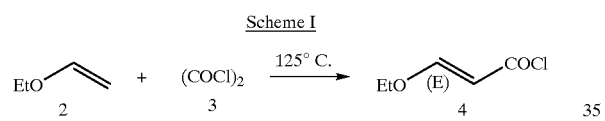

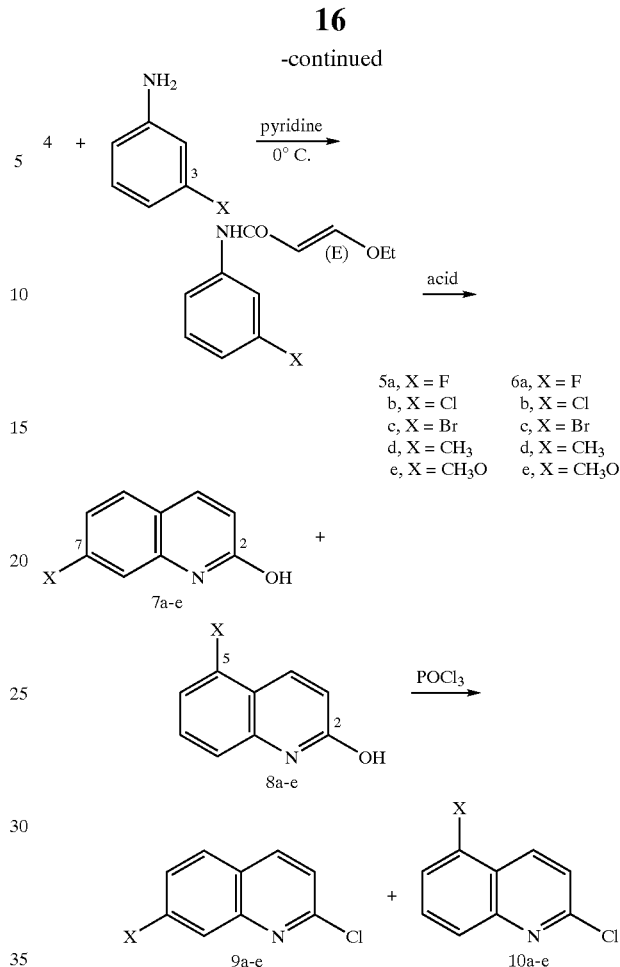

Scheme II

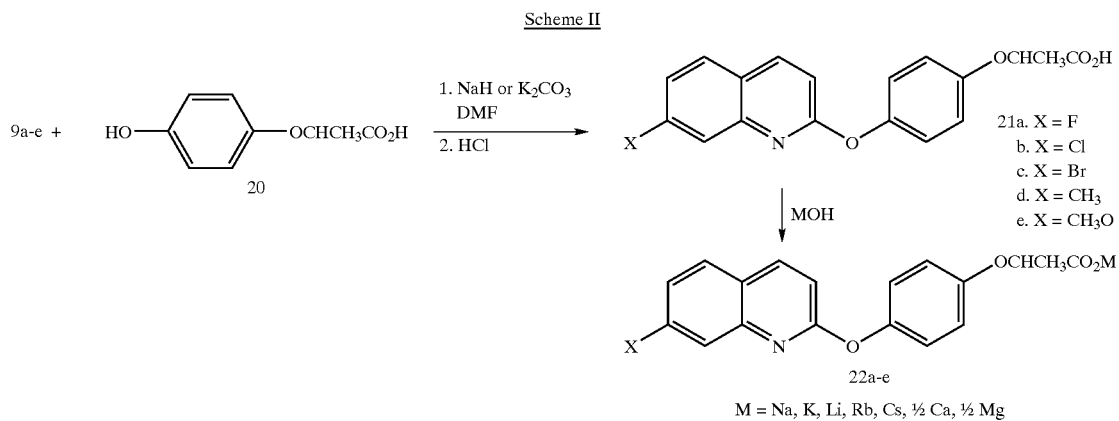

M = Na, K, Li, Rb, Cs, ½ Ca, ½ Mg

As illustrated in Scheme II, the 2-chloroqionolines 9a–e were coupled with 2-(4-hydroxyphenoxy)propionic acid (20) using either NaH or $K_2CO_3$ in refluxing DMF followed by acidification to give the acids (21a–e). These acids can also be converted to their metal salts (22a–e) by reacting with metal hydroxides. XK469, which possesses a single stereogenic center at C-2 of the propionic acid moiety, is generally prepared in the form of a racemic mixture. The R-(+) forms of 21b and 21c were prepared by etherification of commercially available R-(+)-2-(4-hydroxyphenoxy)propionic acid with 9b and c. Chiral HPLC of the R-form of 21b and c, indicated that they had both been obtained in >99% ee (see FIG. 2).

HPLC separations of racemic and R 21b were carried out using ASTEC Chirobiotic T 250×4.6 mm, 65% $H_2O$, 35% $CH_3OH$, 20 mM $NH_4NO_3$ at 1 mL/min with detection at 250 nm.

General Experimental Procedures

To a solution of the 7-substituted-2-chloroquinoline and 2-(4-hydroxyphenoxy)propionic acid (1 eq) dissolved in DMF (5 mL/mmol), 60% NaH (3 eq) was added in portions and the mixture heated at gentle reflux for 2 hours. After cooling it was concentrated to give a solid to which water was added and the solution was filtered through Celite, then washed with water. The filtrate was extracted with ether and the aqueous layer was acidified with 1M HCl to pH 3–4. After cooling, the solid was collected, dried, dissolved in AcOEt and filtered through silica gel. The filtrate was concentrated to a small volume, the solid was collected and recrystallized from AcOEt-heptane.

The reaction can also be carried out using $K_2CO_3$ (2.5 eq) instead of NaH but the reaction times need to be increased to about 12 hours.

2-[4-[(7-Fluoro-2-quinolinyl)oxy]phenoxy]propionic acid 21a (0.14 g, 43% using NaH) as light yellow crystals. mp 135–137° C.; $^1H$ NMR (400 MHz, DMSO-$d_6$) δ 13.08 (bs, 1H), 8.38 (d, J=8.8 Hz, 1H), 7.99 (dd, II=8.8, 6.4 Hz, 1H), 7.40–7.32 (m, 2H), 7.18 (d, J=8.8 Hz, 1H), 7.17–7.12 (m, 2H), 6.94–6.89 (m, 2H), 4.82 (q, J=6.8 Hz, 1H), 1.51 (d, J=6.4 Hz, 3H). $^{13}C$ NMR (75 MHz, DMSO-$d_6$) d 173.9, 163.6 (d, J=245.5 Hz), 163.2, 155.2, 147.6 (d, J=12.7 Hz), 147.3, 141.0, 130.8 (d, J=10.4 Hz), 123.4, 123.2, 116.1, 115.1, (d, J=24.5 Hz), 112.71, 111.7 (d, J=20.8 Hz), 72.5, 19.0. $^{19}F$ NMR (376 MHz, DMSO-$d_6$) δ 76.33 (m). MS (EI) m/z (%) 327 ($M^+$, 59), 282 (15), 268 (15), 254 (67), 238 (8), 226 (4), 209 (4), 198 (3), 151 (5), 146 (100), 126 (12), 119 (7), 91 (7). HRMS (EI) m/z 327.0910 ($M^+$, Calcd for $C_{18}H_{14}NFO_4$ 327.0907).

2-[4-[(7-Chloro-2-quinolinyl)oxy]phenoxy]propionic acid 21b (84% using $K_2CO_3$) as white crystals. mp 149–150° C.; $^1H$ NMR (400 MHz, DMSO-$d_6$) δ 3.05 (bs, 1H), 8.40 (d, J=8.8 Hz, 1H), 7.96 (d, J=8.4 Hz, 1H), 7.66 (d, J=2.8 Hz, 1H), 7.48 (dd, J=8.8, 2.4 Hz, 1H), 7.24 (d, J=8.0 Hz, 1H), 7.18–7.13 (m, 2H), 6.94–6.89 (m, 2H), 4.82 (q, J=6.4 Hz, 1H), 1.51 (d, J=7.2 Hz, 3H). $^{13}C$ NMR (75 MHz, DMSO-$d_6$) δ 173.6, 162.8, 155.0, 147.1, 146.6, 140.6, 135.0, 129.9, 126.1, 125.6, 124.3, 123.0, 116.0, 113.5, 72.4, 18.7. MS (EI) m/z (%) 343 ($M^+$, 46), 298 (15), 284(16), 270 (71), 254 (8), 236 (6), 167 (19), 162 (100), 155 (8), 127 (22), 114 (10), 97 (11), 91 (24), 83 (16), 81 (12), 73 (19), 71 (14), 69 (23), 67 (12), 63 (12), 60 (17), 57 (27), 55 (35), 45 (18). HRMS (EI) m/z 343.0609 ($M^+$, Calcd for $C_{18}H_{14}NClO_4$ 343.0611). Anal. Calcd for $C_{18}H_{14}NClO_4$: C, 62.89; H, 4.10; N, 4.08. Found: C, 63.00; H, 4.18; N, 4.12.

R-(+)-2-[4-[(7-Chloro-2-quinolinyl)oxy]phenoxy]propionic acid was prepared from commercially available R-(+)-2-(4-hydroxyphenoxy)propionic acid. The product was identical in all respects with the racemic product, and exhibited an optical rotation of $[\alpha]^{25}$+19° C. 0.5, 0.1N NaOH).

2-[4-[(7-Bromo-2-quinolinyl)oxy]phenoxy]propionic acid 21c (0.69 g, 70% using NaH) as white crystals. mp 160–161° C.; $^1H$ NMR (400 MHz, DMSO-$d_6$) δ 13.09 (bs, 1H), 8.39 (d, J=8.8 Hz, 1H), 7.88 (d, J=9.2 Hz, 1H), 7.80 (d, J=1.6 Hz, 1H), 7.60 (dd, J=9.2, 1.6 Hz, 1H), 7.25 (d, J=8.8 Hz, 1H), 7.18–7.13 (m, 2H), 6.94–6.89 (m, 2H), 4.82 (q, J=6.8 Hz, 1H), 1.51 (d, J=7.2 Hz, 3H). $^{13}C$ NMR (75 MHz, DMSO-$d_6$) δ 173.9, 163.0, 155.3, 147.2, 147.1, 141.0, 130.3, 129.6, 128.5, 124.9, 124.0, 123.3, 116.1, 114.0, 72.5,19.1. MS (EI) m/z (%) 387($M^+$, 42), 342(10), 328 (10), 314 (31), 300 (6), 285 (7), 256 (22), 236 (13), 206 (53), 199 (18), 185 (10), 171 (8), 157 (8), 127 (44),115 (15), 111(13), 97 (27), 91 (28), 83 (33), 73 (57), 69 (45), 60 (58), 57 (56), 55 (69), 43 (100), 41 (66). HRMS (EI) m/z 387.0107 ($M^+$, Calcd for $C_{18}H_{14}NBrO_4$ 387.0106). Anal. Calcd for $C_{18}H_{14}NBrO_4$: C, 55.69; H, 3.63; N, 3.61. Found: C, 55.52; H, 3.89; N, 3.56.

R-(+)-2-[4-[(7-Bromo-2-quinolinyl)oxy]phenoxy]propionic acid was prepared from commercially available R-(+)-2-(4-hydroxyphenoxy)propionic acid. The product was identical in all respects with the racemic product, and exhibited an optical rotation of $[\alpha]^{25}$+22.0° C. 0.5, 0.1N NaOH).

2-[4-[(7-Methyl-2-quinolinyl)oxy]phenoxy]propionic acid 21d (32% yield from Na) as light yellow crystals. mp 183–185° C.; $^1H$ NMR (400 MHz, DMSO-$d_6$) δ 13.03 (bs, 1H), 8.29 (d, J=8.8 Hz, 1H), 7.78 (d, J=8.0 Hz, 1H), 7.43 (s, 1H), 7.28 (d, J=8.4 Hz, 1H), 7.16–7.10 (m, 3H), 6.93–6.89 (m, 2H), 4.82 (q, J=6.4 Hz, 1H), 2.41 (s, 3H), 1.51 (d,J=6.4 Hz, 3H). $^{13}C$ NMR (100 MHz, DMSO-$d_6$) δ 173.9, 162.4, 155.1, 147.6, 146.6, 140.6 (2C), 128.0, 127.4, 127.0, 124.0, 123.4, 116.1, 112.3, 72.5, 21.9, 19.1. MS (EI) mz (%) 323 ($M^+$, 57), 305 (6), 278 (9), 276 (7), 264 (13), 250 (60), 236 (10), 234 (6), 222 (5), 142 (100), 115 (17), 105 (6), 77 (6). HRMS (EI) m/z 323.1164 ($M^+$, Calcd for $C_{19}H_{17}NO_4$ 323.1158).

2-[4-[(7-Methoxy-2-quinolinyl)oxy]phenoxy]propionic acid 21e (66% yield from $K_2CO_3$) as light yellow crystals. mp 164–166 C; $^1H$ NMR (400 MHz, DMSO-$d_6$) δ 13.06 (bs, 1H), 8.25 (d, J=8.8 Hz, 1H), 7.78 (d, J=8.8 Hz, 1H), 7.16–7.10 (m, 2H), 7.06 (dd, J=8.8,2.4 Hz, 1H), 7.02 (d, J=8.0 Hz, 1H), 6.99 (d, J=2.4 Hz, 1H), 6.94–6.88 (m, 2H), 4.82 (q, J=6.4 Hz, 1H), 3.81 (s, 3H), 1.51 (d, J=7.2 Hz, 3H). $^{13}C$ NMR (100 MHz, DMSO-$d_6$) δ 174.0, 162.9, 161.5, 155.1, 148.3, 147.7, 140.5, 129.5, 123.4, 120.9, 117.5, 116.1, 110.5, 107.0, 72.5, 56.1, 19.1. MS (EI) mz (%) 339 ($M^+$, 62), 323 (10), 294 (8), 280 (13), 266 (35), 250 (13), 175 (7), 158 (100), 142 (18), 115 (10), 77 (6). HRMS (EI) m/z 339.1105 ($M^+$, Calcd for $C_{19}H_{17}NO_5$ 339.1107).

EXAMPLE 2

The following illustrates representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 300.0 |

| (ii) Tablet 2 | mg/tablet |
|---|---|
| 'Compound X' | 20.0 |
| Microcrystalline cellulose | 410.0 |
| Starch | 50.0 |

-continued

| | |
|---|---:|
| Sodium starch glycolate | 15.0 |
| Magnesium stearate | 5.0 |
| | 500.0 |

| (iii) Capsule | mg/capsule |
|---|---:|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---:|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

-continued

| (v) Injection 2 (10 mg/ml) | mg/ml |
|---|---:|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---:|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

TABLE 1

Evaluation Against Early Stage Pancreatic Ductal Adenocarcinoma 03.

| Cage # | Drug IV | # of Inj. | Total dose mg/kg | % Body Wt Loss at Nadir | Day of Nadir | Drug Deaths | Median Tumor Mass on Day 14 (Range) | % T/C mass | Growth Delay in Days | Log Kill | Tumor Free day-37 | Activity Rating |
|---|---|---|---|---|---|---|---|---|---|---|---|---|
| 1 | None | 0 | 0 | +12% | 10 | — | 1513 (681–2149) | — | — | — | 0/5 | - |
| 7 | 22b | 7 | 336 | -8.9% | 11 | 0/5 | 0 (0–126) | 0% | 17.5 | 2.6 | 0/5 | +++ |

TABLE 2

Evaluation Against Early Stage B16 Melanoma.

| Cage # | Drug | # of Inj. | Total dose mg/kg | % Body Wt Loss at Nadir | Day of Nadir | Drug Deaths | Median Tumor Mass on Day 9 (Range) | % T/C mass | Growth Delay in Days | Log Kill | Tumor Free day-24 | Activity Rating |
|---|---|---|---|---|---|---|---|---|---|---|---|---|
| 1 | None | 0 | 0 | +7.4% | 8 | — | 1415 (648–2224) | — | — | — | 0/5 | - |
| 2 | 22b | 8 | 320 | -20.8% | 7 | 1/5 | 0 (all zeros) | 0% | 12.5 | 3.8 | 0.5 | ++++ Toxic |
| 3 | 22b | 5 | 250 | -13.2% | 8 | 0/5 | 0 (all zeros) | 0% | 8.5 | 2.6 | 0/5 | +++ |
| 4 | 22b | 6 | 180 | -7.4% | 5 | 0/5 | 221 (63–334) | 15.6% | 6.0 | 1.8 | 0/5 | ++ |

TABLE 3

Evaluation Against Early Stage Mammary Adenocarcinoma-16/C/Adr.

| Cage # | Drug IV | # of Inj. | Total dose mg/kg | % Body Wt Loss at Nadir | Day of Nadir | Drug Deaths | Median Tumor Mass on Day 11 (Range) | % T/C mass | Growth Delay in Days | Log Kill | Tumor Free day-18 | Activity Rating |
|---|---|---|---|---|---|---|---|---|---|---|---|---|
| 1 | None | 0 | 0 | -2.7% | 7 | — | 1410 (447–3052) | — | — | — | 0/6 | - |
| 2 | 22b | 12 | 504 | -15.0% | 7 | 0/6 | 0 (0–308) | 0% | 8.0 | 2.0 | 0/6 | +++ |
| 3 | 22b | 12 | 324 | -1.1% | 7 | 0/6 | 741 (516–1199) | 53% | 2.25 | 0.6 | 0/6 | - |

TABLE 4

Evaluation of Racemic Compound 22c Against Early Stage Mammary Adenocarcinoma-17/Adr in Female C3H Mice

| Cage # | Drug IV | # of Inj. | Total dose mg/kg | % Body Wt Loss at Nadir | Day of Nadir | Drug Deaths | Median Tumor Mass on Day 10 (Range) | % T/C mass | Growth Delay in Days | Log Kill | Tumor Free day-42 | Activity Rating |
|---|---|---|---|---|---|---|---|---|---|---|---|---|
| 1 | No Rx | 0 | 0 | +1.4% | 9 | — | 3044 (2385–3402) | — | — | — | 0/5 | − |
| 3 | Racemic 22c | 6 | 352.5 | −5.5% | 11 | 0/5 | 0 (0–63) | 0% | 14 | 4.2 | 0/5 | ++++ |
| 4 | Racemic 22c | 6 | 211.5 | −4.1% | 13 | 0/5 | 172 (0–344) | 5.6% | 10 | 3.0 | 0/5 | ++++ |

TABLE 5

Evaluation of the R-Enantiomer of Compound 22b and Compound 22a Against Early Stage Mammary Adenocarcinoma-17/Adr in Female C3H Mice

| Cage # | Drug IV | # of Inj. | Total dose mg/kg | % Body Wt Loss at Nadir | Day of Nadir | Drug Deaths | Median Tumor Mass on Day 9 (Range) | % T/C mass | Growth Delay in Days | Log Kill | Tumor Free day-23 | Activity Rating |
|---|---|---|---|---|---|---|---|---|---|---|---|---|
| 1 | No Rx | 0 | 0 | −2.3% | 6 | — | 960 (828–1357) | — | — | — | 0/5 | − |
| 3 | 22a | 7 | 324 | −1.6% | 5 | 0/5 | 138 (63–207) | 14% | 5 | 1.5 | 0/5 | ++ |
| 4 | 22a | 7 | 162 | −1.5% | 5 | 0/5 | 975 (252–1836) | >100% | 1 | 0.3 | 0/5 | − |
| 5 | 22a | 7 | 81 | −3.0% | 5 | 0/5 | 743 (725–1413) | 77% | 1 | 0.3 | 0/5 | − |
| 6 | R-22b | 4 | 332 | −17.5% | 6 | 5/5 | toxic | toxic | — | — | 0/5 | toxic |
| 7 | R-22b | 4 | 220 | −23.4% | 9 | 1/5 | 0 (all zeros) | 0% | 13 | 3.3 | 0/5 | ++++ |
| 8 | R-22b | 1 | 124.5 | 0 | 9 | 0/1 | 340 (one mouse) | 35% | 3 | 0.8 | 0/1 | + |

TABLE 6

Evaluation of the R-enantiomer of Compound 22b and the R-enantiomer of compound 22c Against Early Staged Mammary Adenocarcinoma-16/C

| Cage # | Drug IV | Schedule days injected | Total dose mg/kg | % Body Wt Loss at Nadir | Day of Nadir | Drug Deaths (days) | Median Tumor Mass on Day 10 (Range) | % T/C mass | Median time for tumors to 1000 mg (range) | Growth Delay in Days | Log Kill | Tumor Free day-155 | Activity Rating |
|---|---|---|---|---|---|---|---|---|---|---|---|---|---|
| 1 | No Rx | — | 0 | +10.4% | 8 | — | 1533 (334–3043) | — | 9.5 (7–12) | — | — | 0/5 | — |
| 2 | R-22c | qd 1–4 | 260 | −22.9% | 6 | 5/5 (6, 6, 7, 7, 7) | toxic | toxic | toxic | toxic | toxic | 0/5 | toxic |
| 3 | R-22c | 1, 3, 5, 7 | 260 | −8.3% | 9 | 0/5 | 63 (0–75) | 4% | 15.3 (14–21.5) | 5.8 | 1.7 | 0/5 | ++ |
| 4 | R-22c | 1, 3, 5, 7 | 160 | +6.4% | 8 | 0/5 | 138 (0–396) | 9% | 14.2 (12.5–16.7) | 4.7 | 1.4 | 1/5 | ++ |
| 5 | R-22b | qd-1–5 | 250 | −22.9% | 8 | 0/5 | 0 (0–138) | 0% | 16.5 (13.5–18) | 7.0 | 2.1 | 0/5 | +++ |
| 6 | R-22b | 1, 3, 5, 7 | 200 | 0% | 8 | 0/5 | 75 (0–171) | 5% | 15.3 (14–17) | 5.8 | 1.7 | 0/5 | ++ |
| 7 | R-22b | 1, 3, 5, 7 | 120 | +6.1% | 8 | 0/5 | 486 (63–509) | 32% | 12 (11.5–14) | 2.5 | 0.8 | 0/5 | + |
| 11 | Adriamycin | 1, 5 | 15 | 0% | 8 | 1/5 (60) | 0 (all zeros) | 0% | 21.5 (17–27.5) | 12.0 | 3.6 | 0/5 | ++++ toxic |

TABLE 7

Evaluation of the R-enantiomers of Compound 22c and 22b Against Up-Staged Pancreatic Ductal Adenocarcinoma-03 in Female BDF1 Mice

| Cg # | Drug | Schedule days injected (route) | Total dose mg/kg | % Body Wt change between day 6 and day 24 | Drug Deaths (days) | Median Tumor Mass on Day 24 (Range) | % T/C mass | Median time for tumors to 1,000 mg (range) | Growth Delay in Days | Log Kill | PR's | CR's | Tumor Free day-157 | Activity Rating |
|---|---|---|---|---|---|---|---|---|---|---|---|---|---|---|
| 1 | No Rx | — | 0 | +14.1% | — | 2259 (1500–3919) | — | 16.5 (15–21) | — | — | 0/6 | 0/6 | 0/6 | — |
| 2 | R-22b | 6, 9, 12, 15, 18, 21, 24 (IV) | 560 | +3.7% | 0/7 | 320 (183–523) | 14.1% | 34 (26–36) | 17.5 | 2.3 | 2/7 | 0/7 | 0/7 | +++ |

TABLE 7-continued

Evaluation of the R-enantiomers of Compound 22c and 22b
Against Up-Staged Pancreatic Ductal Adenocarcinoma-03 in Female BDF1 Mice

| Cg # | Drug | Schedule days injected (route) | Total dose mg/kg | % Body Wt change between day 6 and day 24 | Drug Deaths (days) | Median Tumor Mass on Day 24 (Range) | % T/C mass | Median time for tumors to 1,000 mg (range) | Growth Delay in Days | Log Kill | PR's | CR's | Tumor Free day-157 | Activity Rating |
|---|---|---|---|---|---|---|---|---|---|---|---|---|---|---|
| 3 | R-22b | 6, 9, 12, 15, 18, 21, 24 (IV) | 350 | +8.8% | 0/6 | 658 (235–867) | 29.1% | 28 (23–34) | 11.5 | 1.5 | 1/6 | 1/6 | 0/6 | ++ |
| 4 | R-22b | 6, 9, 12, 15, 18, 21, 24 (IV) | 217 | +10.4% | 0/6 | 1722 (905–2355) | 76.2% | 20 (16–24.5) | 3.5 | 0.5 | 0/6 | 0/6 | 0/6 | − |
| 5 | R-22b | 6, 9, 12, 15, 18, 21, 24 (IV) | 592.8 | +3.5% | 0/5 | 1105 (0–1323) | 48.9% | 23 (23 − >43) | 6.5 | 0.9 | 1/5 | 1/5 | 1/5 | + |
| 12 | R-22b | 6, 9, 12, 15, 18, 21, 24 (IV) | 370.5 | +10.3% | 0/5 | 1868 (0–2148) | 82.7% | 19.5 (17.5 − >43) | 3.0 | 0.4 | 0/5 | 0/5 | 0/5 | − |
| 13 | R-22c | 6, 9, 12, 15, 18, 21 24 (IV) | 480 | +5.9% | 0/4 | 63 (0–196) | 2.8% | 40 (35.5 − >43) | 23.5 | 3.1 | 3/4 | 3/4 | 0/4 | ++++ |
| 8 | Adriamycin | 6, 14 | 15 | +5.4% | 0/5 | 383 (189–400) | 17.0% | 34 (28–35) | 17.5 | 2.3 | 1/5 | 1/5 | 0/5 | +++ |

TABLE 8

Evaluation of the R-enantiomer of XK-469 with the R-enantiomers of Compound 22c
and Compound 22b Against Advanced Staged Colon Carcinoma 26 in Female Balb/c Mice

| Cg # | Rx | Schedule days injected (all IV route) | Total dose mg/kg | % Body Wt change at nadir (day of nadir) | Drug Deaths | Median time for tumors to 700 mg (range) | Growth Delay in Days | Log Kill | PR's | CR's | Tumor Free day-156 | Activity Rating |
|---|---|---|---|---|---|---|---|---|---|---|---|---|
| 1 | No Rx | — | 0 | −9.0% (11)* | — | 13 (11.5–16.5) | — | — | 0/6 | 0/6 | 0/6 | − |
| 3 | 22b(R) | 6, 8, 10, 13, 15 | 250 | −6.2% (16) | 0/6 | 21 (15.5–48) | 8 | 1.4 | 1/6 | 1/6 | 0/6 | ++ |
| 5 | 22c(R) | 6, 8, 10, 13, 15 | 250 | −8.1% (17) | 0/6 | 3/6 tumor free | 3/6 tumor free | >3.5 | 3/6 | 3/6 | 3/6 | ++++ |
| 6 | XK469-R | 6, 8, 10, 14, 16 | 400 | −8.1% (13) | 0/6 | 18 (15–20) | 5 | 0.9 | 0/6 | 0/6 | 0/6 | + |
| 7 | XK469-R | 6, 8, 10, 13, 15 | 250 | −4.0% (13) | 0/6 | 13 (11.5–20) | none | none | 0/6 | 0/6 | 0/6 | − |
| 8 | Cytoxan | 6, 10 | 220 | −9.4% (12) | 0/5 | 14 (12–15) | 1 | 0.2 | 0/5 | 0/5 | 0/5 | − |

What is claimed is:
1. A compound of formula I:

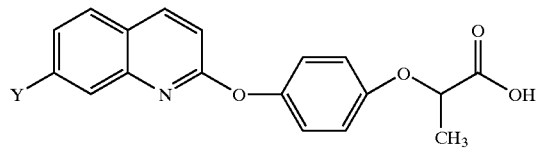

(I)

wherein Y is F, Cl, Br, methyl or methoxy; or a pharmaceutically acceptable salt thereof.
2. The compound of claim 1, wherein Y is F.
3. The compound of claim 1, wherein Y is Cl.
4. The compound of claim 1, wherein Y is Br.
5. The compound of claim 1, wherein Y is —OMe.
6. The compound of claim 1, wherein Y is methyl.
7. The compound of claim 1, wherein the 2-carbon atom of acetic acid is substituted with a methyl group in the (R) configuration.
8. The compound of claim 1, wherein the 2-carbon atom of acetic acid is substituted with a methyl group in the (S) configuration.

9. A compound of claim 1 which is 2-[4-(7-chloroquinolin-2-yloxy)phenoxy]propanoic acid.

10. A compound of claim 1 which is (R) 2-[4-(7-chloroquinolin-2-yloxy)phenoxy]propanoic acid.

11. A composition comprising a compound of, formula (I):

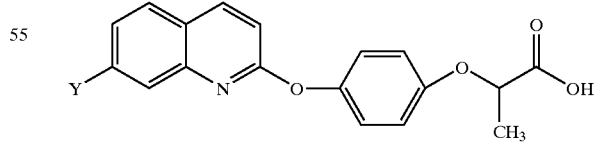

(I)

wherein Y is F, Cl, Br, methyl or methoxy; or a pharmaceutically acceptable salt thereof, in combination with a pharmaceutically acceptable diluent or carrier.

12. A therapeutic method to treat cancer in a mammal, comprising administering to a mammal in need of such therapy an effective amount of a compound of, formula (I):

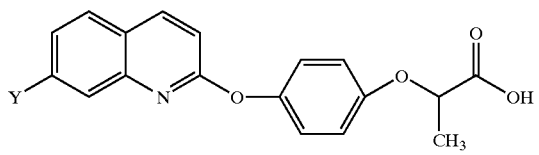

(I)

wherein Y is F, Cl, Br, methyl or methoxy; or a pharmaceutically acceptable salt thereof.

13. The composition of claim 11, wherein Y is F.
14. The composition of claim 11, wherein Y is Cl.
15. The composition of claim 11, wherein Y is Br.
16. The composition of claim 11, wherein Y is —OMe.
17. The composition of claim 11, wherein Y is methyl.
18. The composition of claim 11, wherein the 2-carbon atom of acetic acid is substituted with a methyl group in the (R) configuration.
19. The composition of claim 11, wherein the 2-carbon atom of acetic acid is substituted with a methyl group in the (S) configuration.
20. The composition of claim 11, wherein the compound of formula (I) is 2-[4-(7-chloroquinolin-2-yloxy)phenoxy] propanoic acid.
21. The composition of claim 11, wherein the compound of formula (I) is (R) 2-[4-(7-chloroquinolin-2-yloxy) phenoxy]propanoic acid.
22. The method of claim 12, wherein Y is F.
23. The method of claim 12, wherein Y is Cl.
24. The method of claim 12, wherein Y is Br.
25. The method of claim 12, wherein Y is —OMe.
26. The method of claim 12, wherein Y is methyl.
27. The method of claim 12, wherein the 2-carbon atom of acetic acid is substituted with a methyl group in the (R) configuration.
28. The method of claim 12, wherein the 2-carbon atom of acetic acid is substituted with a methyl group in the (S) configuration.
29. The method of claim 12, wherein the compound of formula (I) is 2-[4-(7-chloroquinolin-2-yloxy)phenoxy] propanoic acid.
30. The method of claim 12, wherein the compound of formula (I) is (R) 2-[4-(7-chloroquinolin-2-yloxy)phenoxy] propanoic acid.
31. The method of claim 12, wherein the cancer is colon cancer, breast cancer, melanoma, pancreatic cancer or leukemia.

* * * * *

UNITED STATES PATENT AND TRADEMARK OFFICE
CERTIFICATE OF CORRECTION

| | | |
|---|---|---|
| PATENT NO. | : 6,867,219 B2 | Page 1 of 1 |
| APPLICATION NO. | : 10/210781 | |
| DATED | : March 15, 2005 | |
| INVENTOR(S) | : Horwitz et al. | |

It is certified that error appears in the above-identified patent and that said Letters Patent is hereby corrected as shown below:

On the title page, in item (56), under "Other Publications", in column 1, line 9, below "Balasubramanian et al. "recent Developments in Cancer, etc.," Annual Reports in Medicinal Chemistry, 33, 1998, Academic Press, San Diego, pp 151-159.*" insert -- Nissan, CA 95:424844 (1981).* --.

On the face page, in item (56), under "Other Publications", in column 2, line 4, delete "2-(4" and insert -- 2-{4 --, therefor.

On the face page, in item (56), under "Other Publications", in column 2, line 5, delete "phenoxy)proplonic" and insert -- phenoxy}propionic --, therefor.

On the face page, in item (56), under "Other Publications", in column 2, lines 9 – 10, delete "2-(4-[97"  and insert -- 2-{4-[(7 --, therefor.

On the face page, in item (56), under "Other Publications", in column 2, line 10, delete "phenoxylproplonic" and insert -- phenoxy}propionic --, therefor.

In column 24, line 50, in Claim 11, after "of" delete ",".

In column 24, line 67, in Claim 12, after "of" delete ",".

Signed and Sealed this

Twenty-fourth Day of April, 2007

JON W. DUDAS
*Director of the United States Patent and Trademark Office*